United States Patent [19]
Schläpfer et al.

[11] Patent Number: 5,520,689
[45] Date of Patent: May 28, 1996

[54] OSTEOSYNTHETIC FASTENING DEVICE

[75] Inventors: Johannes F. Schläpfer, Glarus; Markus Flückiger, Waldenburg, both of Switzerland

[73] Assignee: Synthes (U.S.A.), Paoli, Pa.

[21] Appl. No.: 400,482

[22] Filed: Mar. 8, 1995

Related U.S. Application Data

[63] Continuation of Ser. No. 70,941, Jun. 4, 1993, abandoned.

[30] Foreign Application Priority Data

Jun. 4, 1992 [CH] Switzerland .......................... 01799/92

[51] Int. Cl.⁶ .................................................. A61B 17/70
[52] U.S. Cl. ................................................. 606/61; 606/73
[58] Field of Search .................................. 606/61, 72, 73, 606/57, 59, 54, 60; 623/17

[56] References Cited

U.S. PATENT DOCUMENTS

| | | | |
|---|---|---|---|
| 4,887,596 | 12/1989 | Sherman | 606/61 |
| 5,005,562 | 4/1991 | Cotrel | |
| 5,053,034 | 10/1991 | Olerud | 606/61 |
| 5,176,680 | 1/1993 | Vignaud et al. | |
| 5,190,543 | 3/1993 | Schapfer | 606/61 |
| 5,217,497 | 6/1993 | Mehdian | 623/17 |
| 5,261,907 | 11/1993 | Vignaud et al. | 606/60 |
| 5,261,912 | 11/1993 | Frigg | 606/61 |

FOREIGN PATENT DOCUMENTS

| | | |
|---|---|---|
| 0348272 | 12/1989 | European Pat. Off. . |
| 0441729 | 8/1991 | European Pat. Off. . |
| 2157179 | 10/1985 | United Kingdom . |
| 9116020 | 10/1991 | WIPO . |

Primary Examiner—Stephen C. Pellegrino
Assistant Examiner—Guy V. Tucker
Attorney, Agent, or Firm—Fish & Richardson

[57] ABSTRACT

An osteosynthetic fastening device, preferably in the form of a pedicle screw or a spinal column hook, has a channel in its upper section for receiving a support rod and a retaining element which clamps the rod in the socket through a spherical contact element.

22 Claims, 4 Drawing Sheets

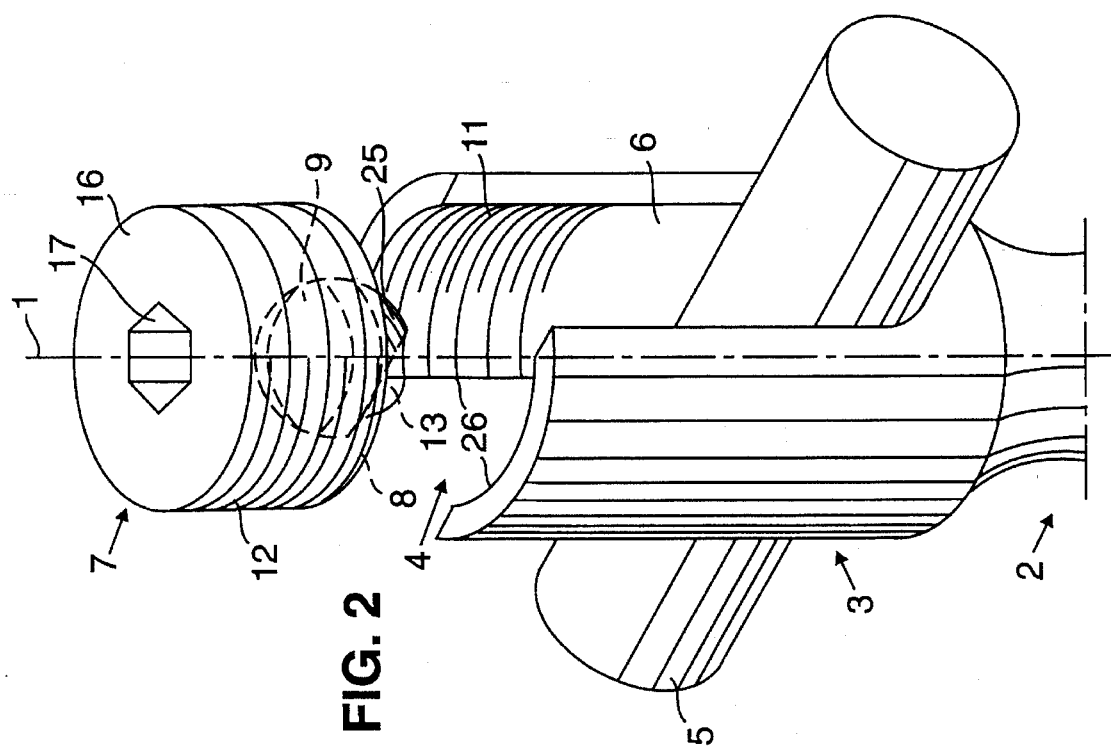
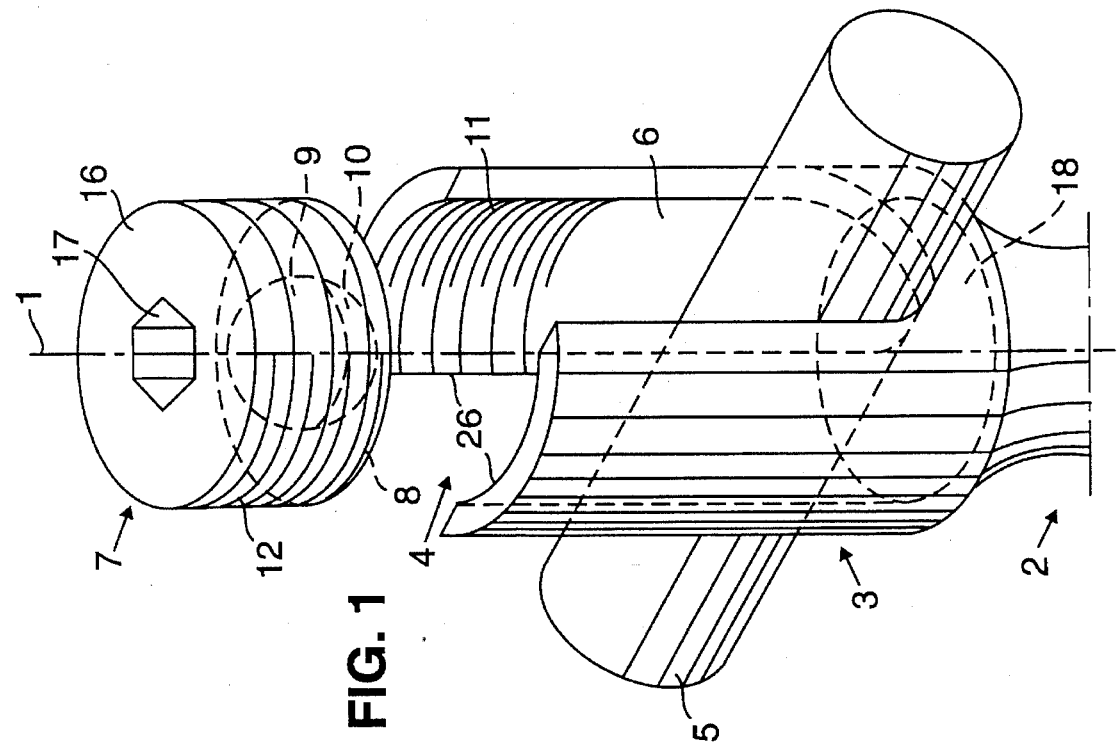

OSTEOSYNTHETIC FASTENING DEVICE

This is a continuation of application Ser. No. 08/070,941 filed on Jun. 4, 1993, now abandoned.

FIELD OF THE INVENTION

The invention concerns an osteosynthetic fastening device, specifically a pedicle screw or a spinal column hook designed to be attached to a support rod.

BACKGROUND OF THE INVENTION

A fastener of this type, of particular application in spinal column surgery, is described in DE-U1 89.15,443.6. In essence that device consists of a lower part having the shape of a screw or a blade for attachment to a bone; and, adjoining the lower part, an upper part for fastening onto a rod. A channel that is open toward the top is formed in the upper part; this channel is bordered by two side walls between which the rod can be contained. Attachment of the rod within the channel is achieved by a threaded stud that can be screwed in. The lower end of this stud, which is meant to be engaged with the rod, is provided with attachment devices in the form of one or more sharp points.

The sharp points that are engaged during screwing in of the threaded stud between the two side walls of the body into the rod positioned there, dig at several locations into the surface of the rod and effect a stable attachment of the rod relative to the body. A disadvantage of this design, however, is that contact between the rod and the threaded stopper is at several separate locations, which can easily loosen if forces are exerted between the rod and the fastening device, as is common in the spinal column area. Forces which affect the rod act through long lever arms on the points which are engaged at separate locations. These lever arms can cause a sudden and irreversible loosening of fixation when very small increments of force are applied.

The invention provides a remedy for this problem by providing an osteosynthetic bone fastener of the type described, which will retain a tight clamping action when forces are applied, or else create a self-clamping effect so that loosening of the parts attached to each other is prevented.

SUMMARY OF THE INVENTION

In accordance with the invention, an osteosynthetic fastening device, useful as a pedicle screw or hook, is provided having a longitudinal axis, a lower portion for attachment to a bone and an upper portion adjoining the lower portion along the longitudinal axis, said upper portion having a transverse channel for receiving a longitudinal support rod, a cylindrical socket with an axis coaxial with said longitudinal axis and a fixation element in said socket, said fixation element having a cavity and a spherical contact element in said cavity, protruding from the bottom of said cavity, thereby to contact a support rod in said transverse channel.

As noted, the fastening element according to the invention has on the lower end of its fixation part a spherical element, located in a cavity and partially protruding from it. The spherical element is preferably movable. As compared to conventional fixation hardware, this design has the advantage of adapting itself automatically to the direction of the rod. Thanks to the geometry of the sphere, which permits compensation by rolling motion, a lasting, continuous clamping effect can be maintained.

The spherical element may be in the form of a segment of a sphere, or a spherical layer, so that support and clamping are linear instead of at discrete points.

If the sphere or partial sphere is movable, then when translational motion between the spherical element and the longitudinal support occurs, because of friction, the sphere seeks to turn, which leads to a skewness and thus even to an increase in the clamping.

In another embodiment of the invention, the spherical element is provided with a concave circular or cylindrical countersink, perpendicular to a radius of the spherical element, to allow an interlocking fit onto the longitudinal support rod. This permits a durable surface contact to be achieved.

In yet another embodiment of the invention, the spherical element is provided with a concave spherical countersink, perpendicular to a radius of the spherical element, for the purpose of allowing an interlocking fit onto a slip-on spherical collar on the longitudinal support rod. If, owing to application of a force to the longitudinal support, the spherical collar tends to turn in any direction, the spherical element with the spherical countersink tends to move in the opposite direction due to friction, which again leads to an increase in the clamping action.

In yet a further embodiment of the invention, an improvement can be achieved by having between the lower section of the longitudinal support rod and the floor of the transverse channel an additional element. For this purpose the floor of the socket is formed with a concave surface in the shape of a circular cylinder, whose cylindrical axis is perpendicular to the longitudinal axis and goes through the center of the sphere (when the sphere is seated on the longitudinal support rod). Between the floor and the longitudinal support rod a tipping piece or part can be placed, whose one convex side corresponds to the surface of the socket, and whose other side, being concave with the shape of a circular cylinder, matches the surface of the longitudinal support rod. The cylindrical axis of the convex side runs perpendicular to the longitudinal support rod. By means of this additional tipping piece, which rotates about the same axis as the sphere, a complete adaptation is possible within a considerable angular range to any changes in angle between the longitudinal support rod and the fastener, without loosening the clamping action between the individual parts.

Preferably in this configuration the floor of the socket is formed either with toothed surface or a wedge geometry. The convex surface of the tipping piece can be shaped in an analogous way. The preferred combinations of surfaces coming into contact with each other are as follows:

| Tipping Piece | Socket |
| --- | --- |
| toothed/hard material | smooth/soft material |
| smooth/soft material | toothed/hard material |
| toothed | toothed |
| wedge-shaped geometry of the longitudinal sides | wedge-shaped geometry of the longitudinal sides |

Preferably the transverse channel is made to be open at the top, in such a way that the upper cutout forms a U-shaped accommodation with two side walls for the longitudinal supports. In this configuration both of the flanks may be secured by a stabilizer cap, since the flanks have a tendency to open up when the fixation hardware is screwed in. For special applications, however, the passageway channel can remain closed at the top, so that no stabilizer socket is necessary.

BRIEF DESCRIPTION OF THE DRAWINGS

The invention will be described further with reference to the accompanying drawings in which:

FIG. 1 is a perspective view of a fastener according to the invention with a sphere as the essential fastening part.

FIG. 2 is a perspective view of another embodiment of the invention with a spherical part as the essential fastening part.

DETAILED DESCRIPTION OF THE PREFERRED EMBODIMENTS

Figure 3:
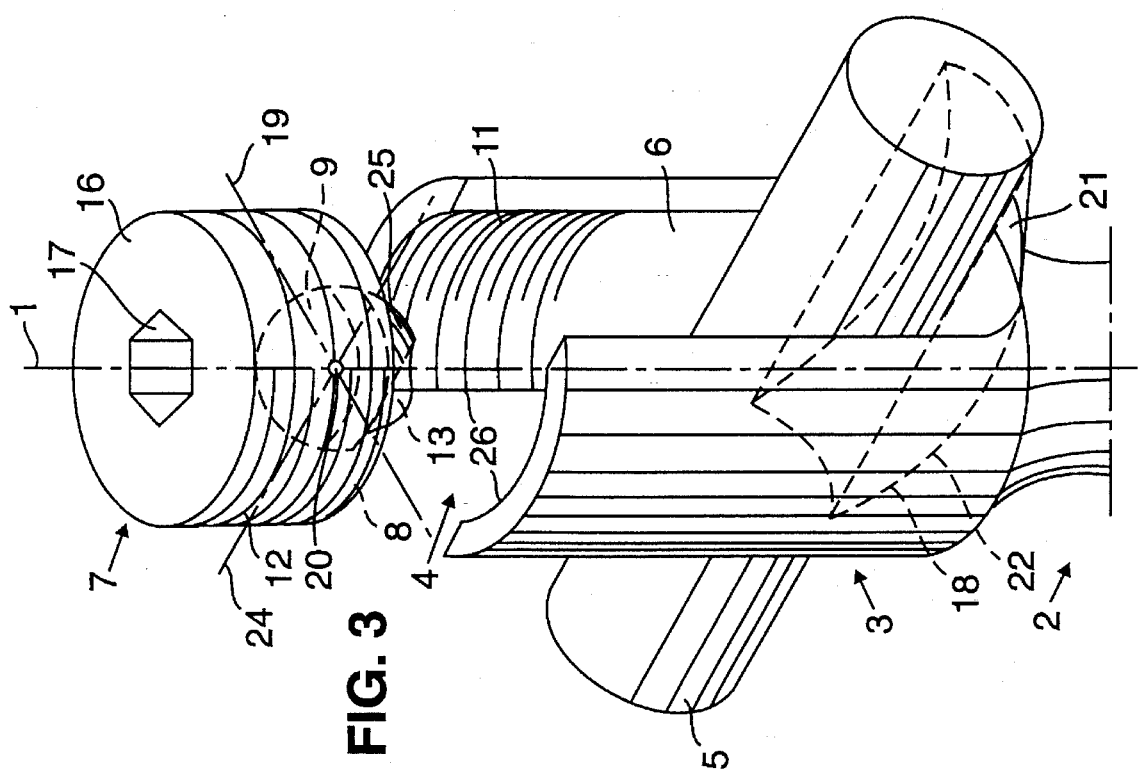
FIG. 3 is a perspective view of an embodiment of the invention with an additional tipping piece.

Referring to FIG. 1, a fastener according to the invention has a bottom portion 2 that can be anchored in bone and an adjoining top portion 3 which is aligned with the longitudinal axis 1 of the fastener. The end of lower portion 2 can be shaped as a screw (e.g. as a pedicle screw) or a curved blade (e.g. a spinal column hook).

The upper portion 3 contains a channel 4 that is open toward the top and is transverse to the longitudinal axis 1. The channel 4 of the upper portion 3 is U-shaped with two side walls 26 facing each other, and a rounded floor in which a longitudinal support rod 5 may be easily inserted. The upper portion of the channel 4 in addition forms a socket 6, shaped like a cylinder parallel to the longitudinal axis 1. On the inside of the socket 6, i.e. on the inner sides of each of the walls 26, an interior thread 11 is provided. For closing the socket 6 and clamping the longitudinal support 5 between the two side walls 26, a fixation element 7 in the form of a circular cylinder is provided. The element 7 has exterior threading 12 which engages the interior threading 11.

On its bottom 8, which is intended to adjoin the longitudinal support rod 5, the fixation element 7 has a cavity 9 which is a segment of a sphere. Into this cavity a sphere 10 is fitted so as to be able to turn. It protrudes partially from the cavity 9.

On its top end 16 the fixation element 7 has a polygonal socket 17 running in the direction of the longitudinal axis 1. Into this socket a suitable instrument such as a hex wrench can be inserted to screw the fixation part 7 into the interior threading 11 between the two side walls 26 and clamp it securely against the longitudinal support 5.

Figure 2A:
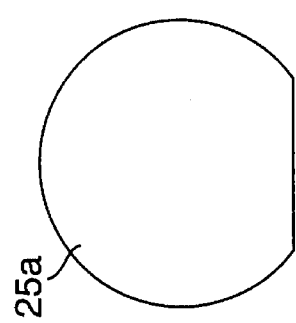
FIG. 2A is an elevational view of a contact element which has a flat contact surface.

Referring to FIG. 2, in another configuration of the fastener according to the invention, in which instead of a full sphere only a spherical part 25 (actually a spherical layer) is provided. The spherical part 25 is either flat on one side shown as 25a in FIG. 2A or has a concave circular-cylindrical countersink 13, perpendicular to its radius, for an interlocking fit with the longitudinal support rod 5. The concave surface 13 is naturally fitted to the surface geometry of the longitudinal support rod 5 that is employed, i.e. it must have the same curvature to achieve the optimum effect, which is to create a durable surface contact between the surface 13 of the spherical part 25 and the longitudinal support rod 5.

Figure 5:
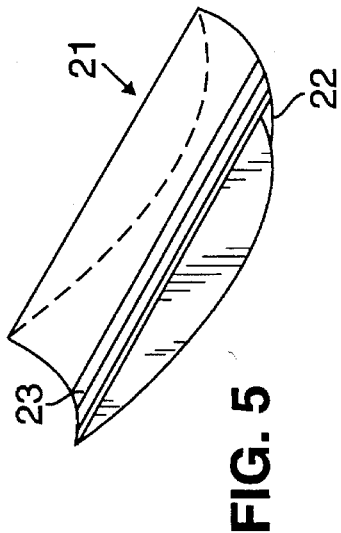
FIG. 5 is a perspective view of the tipping piece of FIG. 3.
Figure 4:
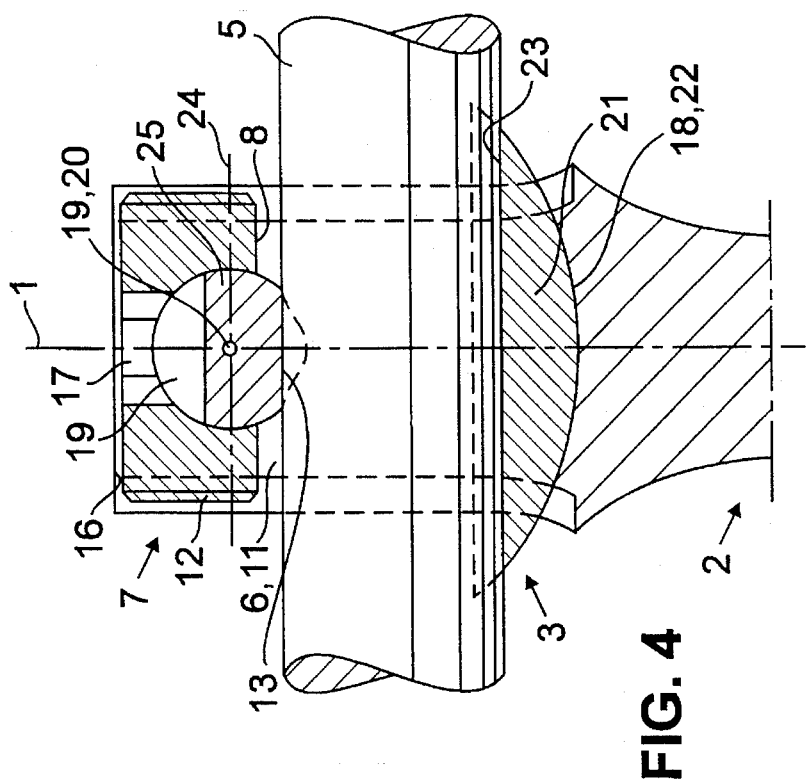
FIG. 4 is a partial longitudinal section through a closed fastener according to FIG. 3.

Referring to FIGS. 3–5, in another embodiment of the invention, the floor 18 of the channel 4 has a concave, cylindrical surface, whose cylindrical axis 19 is perpendicular to the longitudinal axis 1 and through the center 20 of the spherical element 25 (when the element 25 is seated on the support rod 5). An additional tipping part 21 that can be placed between the floor 18 and the longitudinal support rod 5, permits a coaxial rotation synchronized with the spherical part 25. The tipping part 21, which is depicted in detail in FIG. 4, has a convex surface 22 that matches the surface 18 of the channel 4 on one side, and a concave cylindrical surface 23 which matches the surface of the longitudinal support 5. The cylindrical axis of the surface 23 runs perpendicular to cylindrical axis 19. The center of rotation of the tipping piece 21 is identical with the center 20 of the spherical cavity 9 in the fixation part 7, when the fixation part 7 is tightened.

Figure 6:
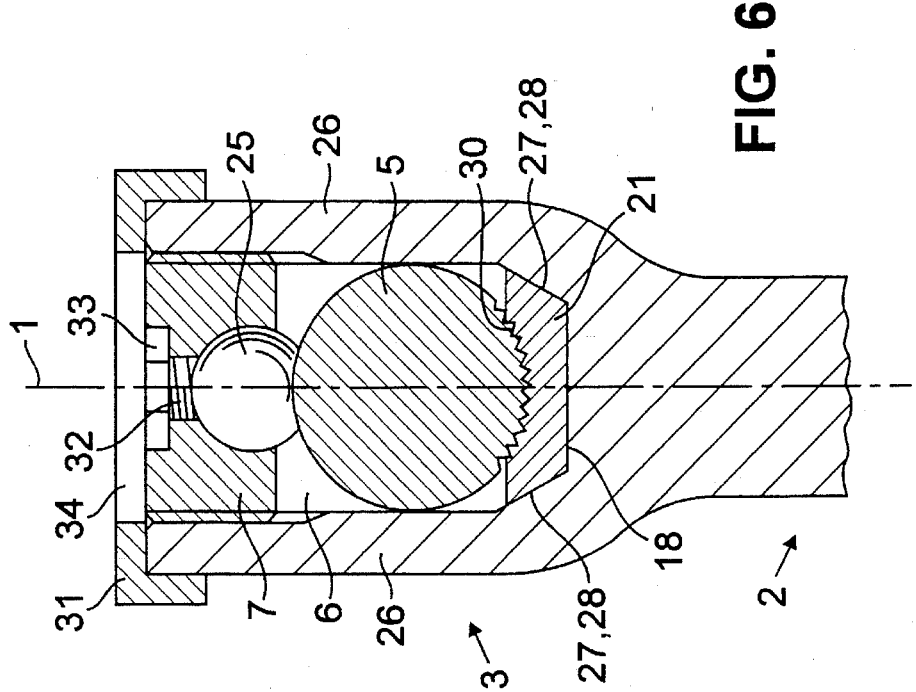
FIG. 6 is a cross section through another embodiment of the invention having a supplementary stabilizer socket.

Referring to FIG. 6, yet another embodiment of the invention has the floor 18 of the channel 4 of the upper portion 3 provided with wedge-shaped walls 27 parallel to the channel 4; matching them are wedge shapes in the outer longitudinal sides 28 of the tipping part 21.

In FIG. 6, the concave surface 23 of the tipping part 21 is provided with longitudinal toothing 29, which corresponds to matching longitudinal toothing 30 of the longitudinal support rod 5, so that after tightening of the fixation part 7, the longitudinal support 5 is protected against torsion.

Lastly, the upper portion 3 has a stabilizer cap 31 that can cover over the two sides 26. It has a central borehole 34, and it protects the two sides 26 from spreading, as can occur when the fixation part 7 is screwed in and tightened.

Instead of having a polygonal slot 17 (FIGS. 1–3), in the configuration of FIG. 6 the fixation element 7 is provided with a threaded bore 32 and a transverse slot 33 for a screwdriver-like instrument. Such a configuration facilitates putting the fixation part 7 in as well as manipulating it and tightening it.

Figure 7:
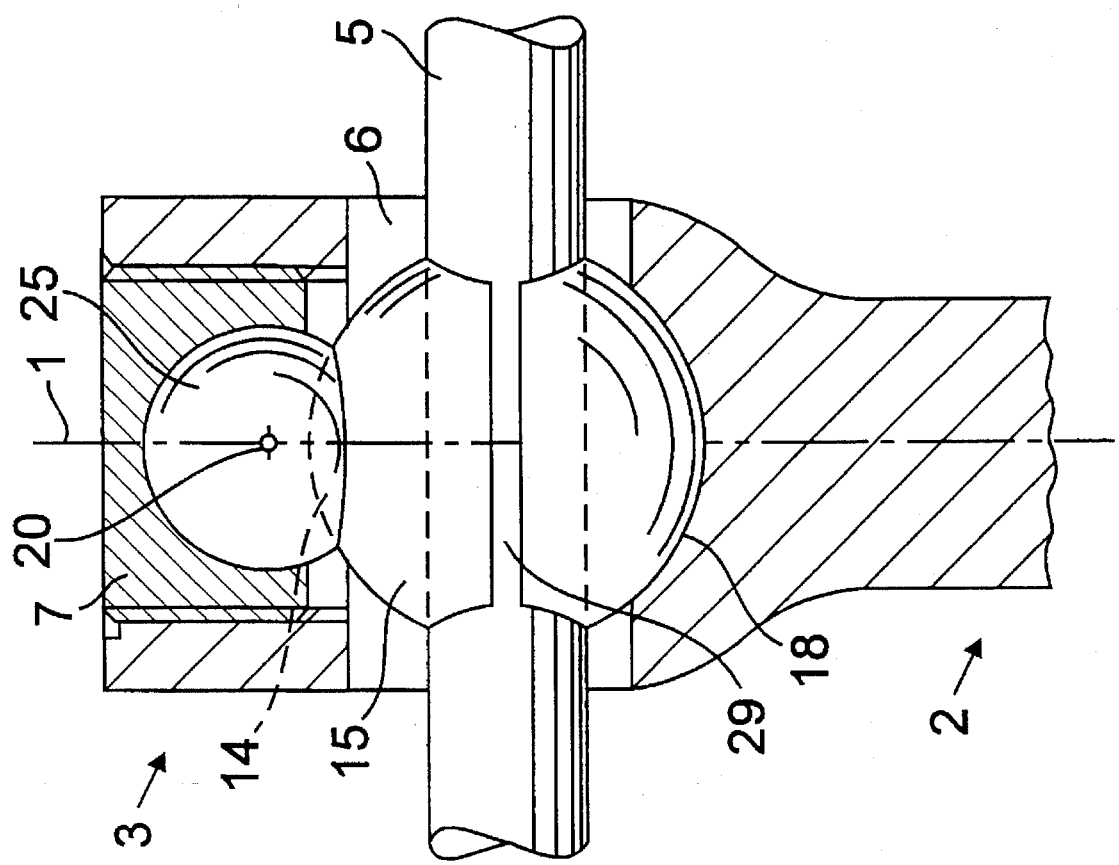
FIG. 7 is a partial longitudinal section through yet another embodiment of the invention with a supplementary collar for a longitudinal support rod.

Lastly, referring to FIG. 7, another embodiment of the fastener according to the invention has a spherical part 25 (here in the form of a spherical segment) equipped with a spherical countersink 14, perpendicular to the radius of the spherical part 25. This countersinking 14 permits an interlocking fit onto a slip-on spherical collar 15 on the longitudinal support rod 5. The collar 15 has a central borehole with a slot 29, to permit a spring-mounted attachment on the longitudinal support rod 5. Also in this configuration the spherical surfaces of the collar 15 and the countersink 14 must be adjusted to each other, i.e., must have the same curvature.

What is claimed is:

1. An osteosynthetic fastening element useful as a pedicle screw or spinal hook, said element comprising, a longitudinal axis, a lower portion for attachment to a bone and an upper portion adjoining the lower portion along the longitudinal axis, said upper portion having a channel transverse to said longitudinal axis for receiving a longitudinal support rod, a cylindrical socket with an axis coaxial with said longitudinal axis and a fixation element in said socket, said fixation element having a cavity and a spheroidal contact element in said cavity and having a portion protruding from the bottom of said cavity, a peripheral part of said portion being cut away to provide a flat or concave surface for contacting a support rod in said transverse channel.

2. The fastener according to claim 1 wherein the socket is provided with interior threading and the fixation element is provided with a matching exterior threading.

3. The fastener according to claim 1 wherein the spheroidal contact element is so situated in the cavity that it can turn.

4. The fastener according to claim 1 wherein the spheroidal contact element is the segment of a sphere.

5. The fastener according to claim 1 wherein the spheroidal contact element is a spherical layer.

6. The fastener according to claim 1 wherein the spherical contact element has a concave cylindrical countersink, perpendicular to a radius of the spherical contact element, forming said surface to provide an interlocking fit onto a longitudinal support rod.

7. The fastener according to claim 1 wherein the fixation element has a polygonal socket on its top side, running parallel to the longitudinal axis to accommodate a fitting tool.

8. The fastener according to claim 1 wherein the fixation element on its top side has a slot running transverse to the longitudinal axis, and a central borehole having interior threading to accommodate a fitting tool.

9. The fastener according to claim 1 wherein:

(A) the bottom of the transverse channel has a concave, cylindrical surface, whose axis is perpendicular to the longitudinal axis;

(B) a tipping part is provided for positioning between the bottom of the transverse channel and a longitudinal support rod in said channel, said tipping part having on one side a convex surface that matches the surface of the bottom of the channel, and on another side a concave, cylindrical surface to fit the surface of a longitudinal support rod;

(C) the center of rotation of said tipping part being identical to the center of rotation of the spheroidal contact element.

10. The fastener according to claim 9 wherein the floor of the transverse channel and the convex surface of the tipping part have toothed surfaces.

11. The fastener according to claim 9 wherein the floor of the transverse channel has a toothed and the tipping part a smooth surface.

12. The fastener according to claim 9 wherein the floor of the transverse channel has a smooth and the tipping part a toothed surface.

13. The fastener according to claim 9 wherein the floor of the transverse channel and the tipping part have smooth surfaces.

14. The fastener according to claim 9 wherein the floor of the transverse channel and the tipping part have irregularly structured surfaces.

15. The fastener according to claim 9 wherein the center of rotation of the tipping part and the spheroidal contact element are at the level of the longitudinal axis of a support rod in said channel.

16. The fastener according to claim 15 wherein the tipping part and the spheroidal contact element are a single element adapted to be slipped on a support rod.

17. The fastener according to claim 15 wherein the tipping part is spheroidal and the tipping part and the spheroidal contact collar-like element adapted to be slipped on the support rod.

18. The fastener according to claim 9 wherein the center of rotation of forms is located to be on top of a support rod positioned in said channel.

19. The fastener according to claim 9 wherein the floor of the socket and the tipping part are wedge-shaped.

20. The fastener according to claim 1 wherein the transverse channel is open at the top to form a U-shape having two sides for a longitudinal support rod.

21. The fastener according to claim 20 and comprising a stabilizer cap mountable over the two sides.

22. A fastening system for use in osteosynthesis comprising a support rod and a fastening element adapted for use as a pedicle screw or spinal hook, said fastening element having a longitudinal axis, a lower portion for attachment to a bone and an upper portion adjoining the upper portion along the longitudinal axis, said upper portion having a transverse channel for receiving said support rod, a cylindrical socket with an axis coaxial with said longitudinal axis and a fixation element in said socket, said fixation element having a cavity and a spheroidal contact element in said cavity, said contact element having a peripheral part cut away to provide a flat or concave surface for contacting the support rod in said channel.

* * * * *

UNITED STATES PATENT AND TRADEMARK OFFICE
CERTIFICATE OF CORRECTION

PATENT NO. : 5,520,689

DATED : May 28, 1996

INVENTOR(S) : Johannes F. Schlapfer & Markus Flukiger

It is certified that error appears in the above-identified patent and that said Letters Patent is hereby corrected as shown below:

Claim 16, line 2, delete "and the spheroidal contact element are a single element" and insert --is--.

Claim 17, lines 2 & 3, delete "and the tipping part and the spheroidal contact" and insert --forms a--.

Claim 18, line 2, after "rotation of" delete "forms" and insert --the tipping part--.

Signed and Sealed this

Tenth Day of March, 1998

*Attest:*

BRUCE LEHMAN

*Attesting Officer*     Commissioner of Patents and Trademarks